United States Patent [19]

Van Kampen

[11] Patent Number: 4,673,409

[45] Date of Patent: Jun. 16, 1987

[54] IMPLANT WITH ATTACHMENT SURFACE

[75] Inventor: Craig L. Van Kampen, St. Paul, Minn.

[73] Assignee: Minnesota Mining and Manufacturing Company, St. Paul, Minn.

[21] Appl. No.: 844,874

[22] Filed: Mar. 27, 1986

Related U.S. Application Data

[62] Division of Ser. No. 603,777, Apr. 25, 1984, Pat. No. 4,608,052.

[51] Int. Cl.[4] ............................ A61F 2/36; B23K 9/00
[52] U.S. Cl. ........................................ 623/23; 623/16;
   623/22; 219/121 LL; 219/121 LN; 219/121 EM; 219/121 PB; 219/121 PE
[58] Field of Search ............... 219/121 LK, 121 LL, 219/121 LN, 121 EM, 121 PB, 121 PC, 121 PE; 623/16, 66, 22, 23

[56] References Cited

U.S. PATENT DOCUMENTS

| | | | |
|---|---|---|---|
| 3,226,527 | 12/1965 | Harding | 219/384 |
| 3,404,254 | 10/1968 | Jones | 219/121 |
| 3,588,439 | 6/1971 | Heller et al. | 219/121 |
| 3,594,292 | 7/1971 | Russell et al. | 204/143 |
| 3,605,123 | 9/1971 | Hahn | 3/1 |
| 3,649,806 | 3/1972 | Konig | 219/121 |
| 3,808,606 | 5/1974 | Tronzo | 3/1 |
| 3,855,638 | 12/1974 | Pilliar | 3/1 |
| 3,890,107 | 6/1975 | White et al. | 29/183 |
| 4,028,523 | 6/1977 | Anderl et al. | 219/121 EM |
| 4,272,855 | 6/1981 | Frey | 3/1.9 |
| 4,330,891 | 5/1982 | Branemark et al. | 3/1 |
| 4,361,630 | 11/1982 | Johnson, Sr. | 428/613 |

FOREIGN PATENT DOCUMENTS

| | | |
|---|---|---|
| 0047231 | 8/1981 | European Pat. Off. . |
| 0098224 | 6/1983 | European Pat. Off. . |
| 837294 | 7/1949 | Fed. Rep. of Germany . |
| 2205808 | 2/1972 | Fed. Rep. of Germany . |
| 31191304 | 5/1981 | Fed. Rep. of Germany . |
| 8127991 | 9/1981 | Fed. Rep. of Germany . |
| 2194123 | 7/1972 | France . |

OTHER PUBLICATIONS

Ion—Beam Microtexturing of Biomaterials by George J. Picha and Dennis J. Siedlak, *Medical Device and Diagnostic Industry*, Apr., 1984, pp. 39–42.

*Primary Examiner*—Richard J. Apley
*Assistant Examiner*—Alan W. Cannon
*Attorney, Agent, or Firm*—Donald M. Sell; James A. Smith; Robert W. Hoke, II

[57] ABSTRACT

An implant for use in a human body having an integral attachment surface adapted to permit tissue ingrowth. The attachment surface has an inner attachment surface and a multiplicity of spaced posts projecting from the inner attachment surface. The posts each have side attachment surfaces which are generally cylindrically concave, intersect to define post edges, and are radiused at their intersections with the inner attachment surface. A method of forming the attachment surface on an implant with a laser is also included.

8 Claims, 10 Drawing Figures

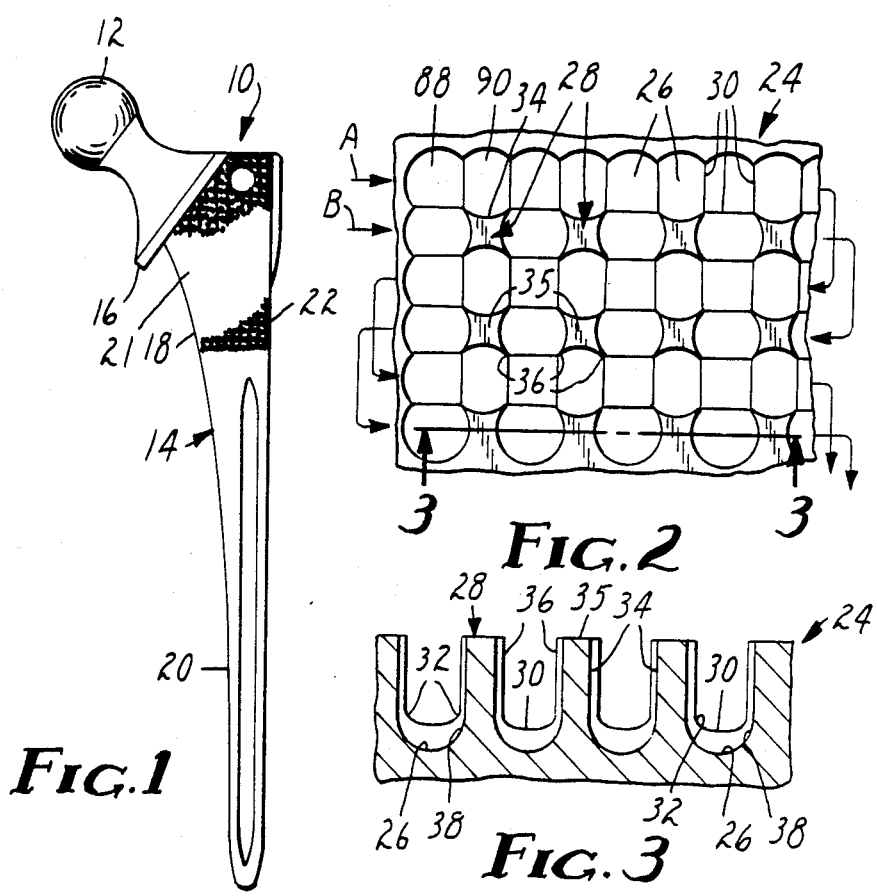
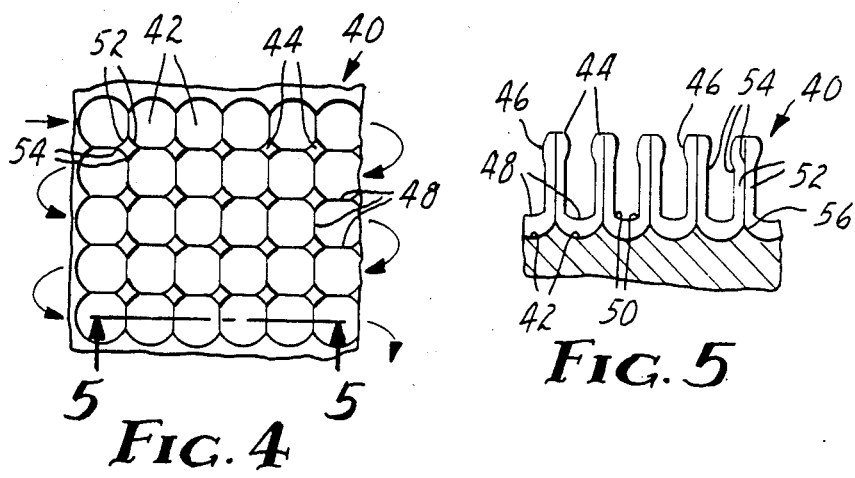

IMPLANT WITH ATTACHMENT SURFACE

This is a division of application Ser. No. 603,777 filed Apr. 25, 1984, now U.S. Pat. No. 4,608,052.

BACKGROUND

The invention relates to the field of implants for use in a human body and, more particularly, to an implant having an integral attachment surface adapted to permit tissue ingrowth. A method of forming an attachment surface on an implant with a laser is included within the scope of the invention.

Many methods and devices have been developed to improve the fixation of an implant in the body so that the implant becomes as permanent as possible. One method well known in the area of orthopedic implants is the use of cements such as polymethylmethacrylate to anchor the implant. Another way to improve the permanence of implants is to construct the implants so as to receive an ingrowth of body tissue. For example, implants have been provided with porous surfaces as described in U.S. Pat. Nos. 3,605,123, 3,808,606 and 3,855,638.

U.S. Pat. No. 4,272,855 questoins the merit of implants having porous surfaces implying that the mechanical strength of the implant is reduced by sharp corners and edges associated with such anchoring surface. According to this patent, these sharp corners and edges can lead to the formation of cracks, which may continue into the solid core of the implant and eventually lead to fatigue failures. It is disclosed that this disadvantage can be overcome with an anchoring surface which includes a plurality of depressions or projections devoid of corners and edges. The anchoring surface is described as produced by embossing, cast molding, chemical etching, milling or another mechanical kind of machining.

It is not believed that a surface devoid of corners and edges is best suited for tissue ingrowth. While a generally rounded surface does minimize the formation of stresses within the implant, it also minimizes the total surface area that can be contacted by the tissue. This reduction of surface area significantly reduces the strength of the attachment of the implant to the tissue, which is nearly totally dependent upon the mechanical interaction of the implant and the tissue. This mechanical interaction is generally of two types. One is a form of interlocking to the extent the tissue grows behind or around a part of the implant. The other is frictional, wherein the tissue grows into intimate approximation with the surface and results in a relatively tight frictional fit.

The anchoring surface of U.S. Pat. No. 4,272,855 minimizes the strength of both of these mechanical interactions. A totally rounded surface provides little structure into which the tissue can interlock. Furthermore, a totally rounded surface minimizes the area that can contact the tissue and frictionally restrict relative movement between the implant and the tissue. the implant of the present invention overcomes these disadvantages while still minimizing the creation of internal stresses within the implant due to sharp edges and corners.

SUMMARY OF THE INVENTION

According to the invention, there is provided an implant for use in a human body. The implant has an integral attachment surface that is adapted to permit ingrowth of living tissue. The implant surface is defined by a multiplicity of adjacent, generally concave surface parts having intersecting, generally aligned rims defining an inner attachment surface portion and by a multiplicity of spaced posts projecting from said inner attachment surface portion. The posts each have a plurality of side attachment surfaces. The side attachment surfaces are generally cylindrically concave about mutually parallel axes, intersect to define generally sharp, mutually parallel post edges, and are radiused at their intersections with said side attachment surfaces.

According to the invention, there is also provided a method of forming an attachment surface on an implant for use in a human body. The method comprises the steps of directing a pulsating beam of laser energy towards a surface of the implant and moving the beam of laser energy relative to the surface in a predetermined pattern to drill a multiplicity of generally cylindrical bores in the surface to form the attachment surface.

BRIEF DESCRIPTION OF THE DRAWINGS

The present invention will be further described with reference to the following drawings wherein the numerals refer to like parts.

FIG. 1 is a plan view of an implant having an attachment surface according to the present invention.

FIG. 2 is an enlarged plan view of one embodiment of a portion of the attachment surface of FIG. 1.

FIG. 3 is a cross-sectional view taken approximately along line 3—3 of FIG. 2.

FIG. 4 is an enlarged plan view of a second embodiment of a portion of the attachment surface of FIG. 1.

FIG. 5 is a cross-sectional view taken approximately along line 5—5 of FIG. 4.

DETAILED DESCRIPTION

Figure 8:
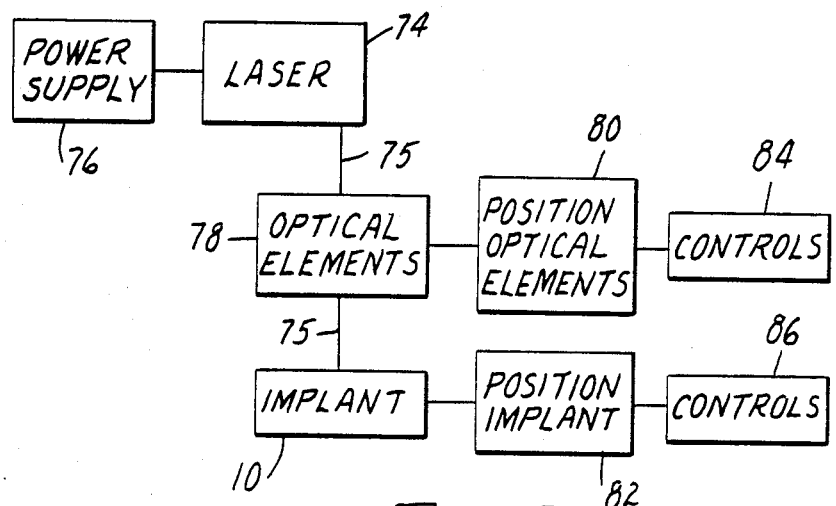
FIG. 8 is a schematic illustration of an implant and apparatus for forming an attachment surface on the implant.

Referring now to FIG. 1 of the drawings, there is shown in plan view an implant 10. The implant 10 is a stemmed femoral component for a human hip. The implant 10 is used to replace a natural femoral head that has been removed prior to insertion of the implant. The methods of removal of the natural femoral head and insertion of the implant 10 are conventional and well known in the art. The implant 10 is conventionally comprised of a metal alloy such as a cast cobalt and chrome alloy made to American Society for Testing and Materials, Standard No. 75. Although the implant 10 is shown and will be described as the stemmed femoral head, the implant of the invention can take on many other forms, and nothing herein is meant to limit the invention to a stemmed femoral head implant. For example, the implant can also be an acetabular component of hip prostheses, a humeral or a glenoid component of shoulder prostheses, a femoral or a tibial component of knee prostheses, anchoring plugs or devices for attaching ligaments or tendons to bones, bone repair devices for bone grafting or segmental bone replacement, finger joint grommets, or tooth root implants. Similarly, the implant can be comprised of other materials including wrought cobalt-chrome alloys, titanium-6 aluminum-4 vanadium alloy, stainless steel alloys, ultrahigh molecular weight polyethylene, and ceramics such as alumina. While the above implants relate primarily to orthopedic applications, the list is not exhaustive, and nothing herein is meant to limit the invention to orthopedic applications or to limit the materials to those listed. For example, other biomedical applications for which it can be desirable to morphologically alter implant surfaces to permit tissue ingrowth include percutaneous connectors, pacemaker housings, cardiovascular prostheses, and soft tissue implants in general in which implant stabilization is required. Such other biomedical applications can encompass the use of materials in the general classes of fluoropolymers, silicone polymers, polyacetals, polyurethanes, polysulfones, polyaramids, polyesters, and polyolefins.

The implant 10 includes a femoral head 12 and a femoral stem 14 which is adapted to be inserted into a medullary canal of a femur. The stem 14 includes a collar 16, a metaphyseal portion 18 and a diphyseal portion 20. The collar 16 is adapted to rest on cortical bone in the regions of the natural femoral neck. The metaphyseal portion 18 is adapted to contact a metaphyseal area of the femur in conventional fashion. The diphyseal portion 20 is adapted to conventionally contact a corresponding portion of the femur.

An attachment surface 22 is preferably provided on a front side 21 and a like back side, not shown, of the metaphyseal portion 18. A portion 24 of one embodiment of the attachment surface 22 is shown in FIG. 2. The portion 24 is defined by a multiplicity of generally part-spherical, concave surface parts 26 and a multiplicity of elongate, preferably equal-length posts 28. The surface parts 26 are adjacent each other and have intersecting, generally aligned rims 30 as also shown in FIG. 3.

Referring to FIG. 2 and FIG. 3, the intersecting, generally aligned rims 30 define an inner attachment surface portion 32. Projecting from the inner attachment surface portion 32 are the posts 28. Each of the posts 28 has four side attachment surfaces 34 and an end surface 35. The end surfaces 35 define an outer attachment surface. The outer attachment surface 35 is generally flush with the adjacent surface of the implant 10. Each of the side attachment surfaces 34 is generally cylindrically concave about an axis preferably perpendicular to the inner attachment surface portion 32. The side attachment surfaces 34 intersect to define four generally sharp post edges 36 per each post 28. The post edges 36 are generally mutually parallel and preferably extend generally perpendicular to the inner attachment surface portion 32. The side attachment surfaces 34 are radiused at their intersections 38 with the concave surface parts 26. The intersections 38 between the concave surface parts 26 and the posts 28 are radiused to eliminate stress risers there between. Stress risers are well known to be sharp corners where stresses are concentrated due to geometric considerations. A high concentration of stress leads to an increased likelihood of cracks which can lead to fatigue failure.

Although the intersections 38 are radiused, the side attachment surfaces 34 of each post 28 are cylindrically concave and intersect at relatively sharp post edges 36. These cylindrically-concave side attachment surfaces 34 have distinct advantages over rounded surfaces. Posts 28 having cylindrically-concave side attachment surfaces 34 provide a concave space on all sides of each post 28 for local tissue ingrowth, which increases stabilization of the implant 10 by means of localized mechanical interlocking. Such interlocking is not possible with totally rounded surfaces. In addition, the cylindrically-concave posts 28 provide increased surface area for frictional resistance to forces tending to separate the tissue from the implant 10.

Comparing posts 28 having cylindrically-concave side attachment surfaces 34 with totally rounded surface projections, one can readily calculate the respective surface areas. Since frictional resistance is directly proportional to surface area, the relative increase in frictional resistance associated with the cylindrically-concave side attachment surfaces 34 can be determined.

Assuming a center-to-center spacing of posts or surface projections equal to 500 microns and a post or surface proejction height of 450 microns, the surface areas can be calculated as follows. The totally rounded surface projections can be approximated as three separate portions: a top portion represented by a 150 micron diameter hemisphere, a middle portion represented by a frustrum of a cone having a 250 micron height and top and bottom base diameters of 150 and 250 microns, respectively, and a base portion represented by another frustrum of a cone having a 125 micron height and top and bottom base diameters of 250 and 400 microns, respectively. The surface areas of these portions are calculated by standard mensuration formulas to give a total surface area of 0.344 mm$^2$ for a single totally rounded surface projection. The posts 28 with cylindrically-concave side attachment surfaces 34 can also be approximated by three separate portions: a top portion represented by a 300 micron square less four circular segments having a 300 micron cord length and a rise of 50 microns, a middle portion represented by four circular arc lengths having a 300 micron cord length and a rise of 50 microns and each having a height of 325 microns, and a base portion represented by a frustrum of a cone having a 125 micron height and top and bottom base diameters of 225 microns and 325 microns, respectively. Again, standard mensuration formulas are used to calculate a total surface area of 0.605 mm$^2$ for a single post 28 with cylindrically-concave side attachment surfaces 34. This is an increase of 1.76 times more surface area and results in 76% more frictional resistance to forces at the interface to improve the anchoring of implants having posts 28 with cylindrically-concave side attachment surfaces 34 as compared to implants with totally rounded surfaced projections. The enhanced mechanical interlocking and frictional resistance of the posts 28 having cylindrically-concave side attachment surfaces 34 resist torsional forces to which the implant 10 is subjected after implantation into the body. Torsional forces are significant, for example, with hip implants due to the tendency of the implant to toggle. Such forces can be a primary contributor to loosening and failure of hip implants.

In addition to resisting torsional forces at the interface of the implant 10 and the tissue, the tissue attachment surface 22 must also resist forces generally perpendicular to the interface that would otherwise tend to pull the tissue directly away from the implant 10. Initially, the posts 28 with the cylindrically-concave side attachment surfaces 34 provide 76% more surface area and thus 76% more resistance to separation of the tissue from the implant 10 when forces normal to the interface are experienced. Subsequent to the initial microscopic separation of the tissue from the implant 10, the cylindrically-concave side attachment surfaces 34, which are preferably generally perpendicular to the inner attachment surface portion 32 and, hence, generally perpendicular to the implant/tissue interface, continue to provide frictional resistance to further separation of the tissue from the implant 10. Rounded surface projections, on the other hand, provide no frictional resistance to perpendicular separation of the tissue from the implant 10 after the initial microscopic separation. Specifically, for the post dimensions described above, the four cylindrically-concave side attachment surfaces 34 of each post 28 provide 0.418 $mm^2$ of surface area for frictional resistance to forces normal to the surface. Thus, in 1 $cm^2$ of planar surface area the posts of the present invention provide 167 $mm^2$ of perpendicular surface area to resist normal forces at the interface.

The multiplicity of concave surface parts 26 and the posts 28 define the attachment surface 22. The attachment surface 22 is adapted to permit ingrowth of living tissue by proper dimensioning of the surface parts 26 and the posts 28. It is well documented in the literature that biological tissue will grow into recesses within materials conventionally used to fabricate implants and will remain viable therein if the recesses are of an adequate size to support vascularization. The minimum recess size necessary for hard tissue, i.e., primarily bone, ingrowth is generally considered to be about 150 microns. Soft tissue, such as skin and fascia, will grow into recesses at least as small as 50 microns. The depth of tissue ingrowth into an implant 10 is theoretically unlimited given adequate space for vascularization and acceptable biochemical and biomechanical compatibility between the implant 10 and the ingrown tissue. Hence, it is preferred that the part-spherical, concave surface parts 26 each have a diameter in the range of about 50-150 microns for soft tissue implants and 200-400 microns for hard tissue implants. It is also preferred, with the embodiment shown in FIG. 2 and FIG. 3, that each of the posts 28 has a transverse width in the range of about equal to the diameter of the concave surface parts 26.

Figure 9:
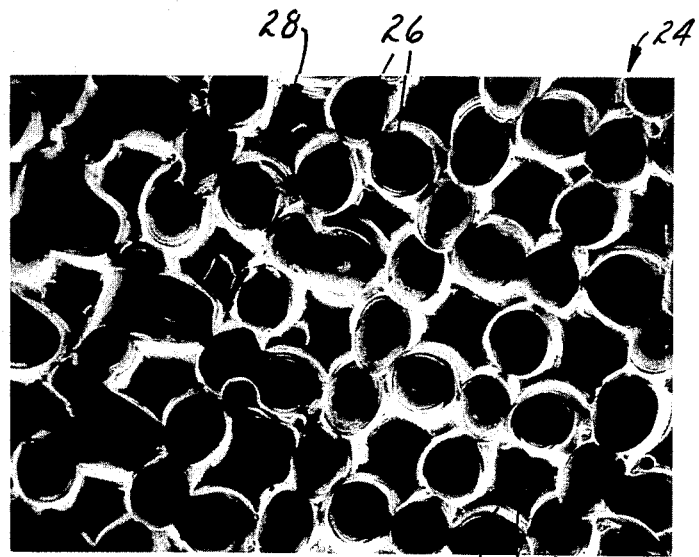
FIG. 9 is a scanning electron micrograph similar to the plan view of FIG. 2 at a magnification of 50 times.
Figure 10:
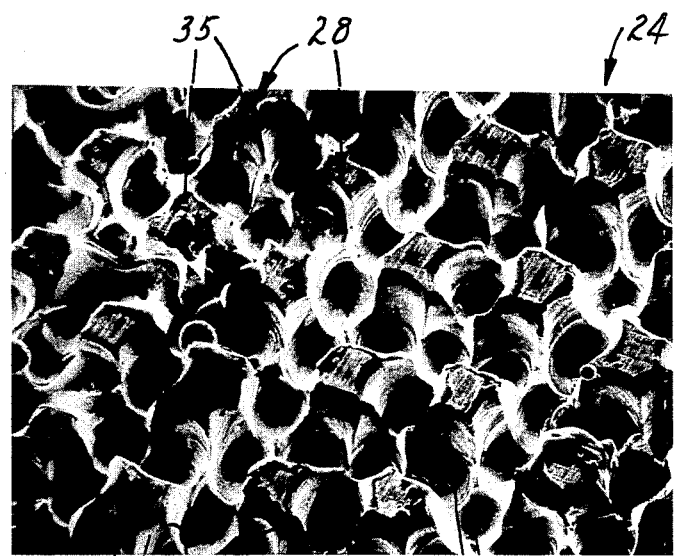
FIG. 10 is a scanning electron micrograph similar to FIG. 9 except that the micrograph was taken at an angle of 30 degrees from the view of FIG. 9.

FIG. 9 is a scanning electron micrograph of the plan view of FIG. 2 at a magnification of 50 times. FIG. 9 shows the individual concave surface parts 26 and the posts 28 as formed by a method described below. FIG. 10 is a scanning electron micrograph similar to FIG. 9 except that the micrograph of FIG. 10 was taken at an angle of 30 degrees from the view of FIG. 9. FIG. 10 shows the cylindrically-concave side attachment surfaces 34 of the posts 28. The scanning electron micrographs of FIG. 9 and FIG. 10 show certain irregularities in the structure of the portion 24. These irregularities result from the method of manufacture as will be described.

One such irregularity can be protrusions extending from various locations on the posts, e.g. at the top, along the rim, or on the sides. Such protrusions can be advantageous in that they provide undercut areas for enhanced interlocking between the implant and the tissue. A portion 40 of a second embodiment of the attachment surface 22 is shown in a plan view in FIG. 4 and in a cross-sectional view in FIG. 5. FIG. 5 shows a multiplicity of generally part-spherical, concave surface parts 42 and a multiplicity of elongate posts 44 similar to the posts 28 of FIG. 2 and FIG. 3. A difference is a width-increasing protrusion 46 located on the free end of each of the posts 44. The protrusions 46 are bulbous shaped and are caused by a method by which the attachment surface 22 is formed and will be described in detail later.

As with the portion 24 of FIGS. 2 and 3, the portion 40 of FIGS. 4 and 5 joins the surface parts 42 with intersecting, generally aligned rims 48 to define an inner attachment surface portion 50. Projecting from the inner attachment surface portion 50 are the posts 44. Each of the posts 44 has four side attachment surfaces 52. The side attachment surfaces 52 are generally cylindrically-concave about mutually parallel, longitudinally aligned axes and are preferably generally perpendicular to the inner attachment surface portion 50. The side attachment surfaces 52 intersect in a manner different from that of FIGS. 2 and 3 to define four post edges 54 per each post 44. The difference is related to a method by which the portion 40 is formed and will be described in detail later. The post edges 54 are generally mutually parallel, longitudinally aligned and preferably extend generally perpendicular to the inner attachment surface portion 50. The side attachment surfaces 52 are radiused as before at their intersections 56 with the concave surface parts 42.

Figure 6:
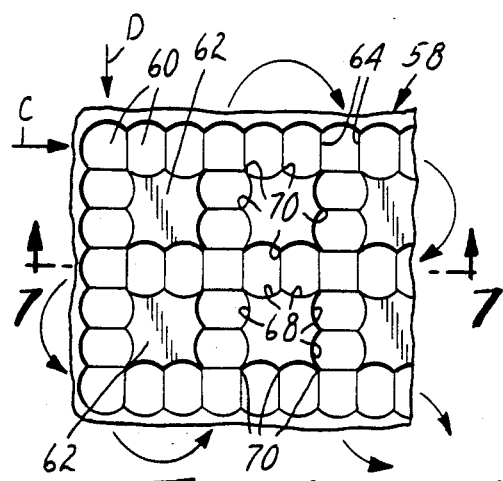
FIG. 6 is an enlarged plan view of a third embodiment of a portion of the attachment surface of FIG. 1.
Figure 7:
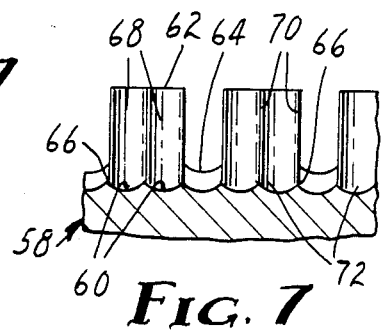
FIG. 7 is a cross-sectional view taken approximately along line 7—7 of FIG. 6.

A portion 58 of a third embodiment of the attachment surface 22 is shown in a plan view in FIG. 6 and in a cross-sectional view in FIG. 7. FIG. 7 shows a multiplicity of generally part spherical, concave surface parts 60 and a multiplicity of posts 62 similar to the posts 28 of FIGS. 2 and 3 and to the posts 44 of FIGS. 4 and 5. As with the portions 24 and 40 of FIGS. 2 and 3 and FIGS. 4 and 5, respectively, the portion 58 joins the surface parts 60 with intersecting, generally aligned rims 64 to define an inner attachment surface portion 66. Projecting from the inner attachment surface portion 66 are the posts 62. Each of the posts 62 has eight side attachment surfaces 68. Each of the side attachment surfaces 63 is generally cylindrically-concave about an axis preferably perpendicular to the inner attachment surface portion 66. The side attachment surfaces 68 intersect in a manner different from that of FIGS. 2 and 3 and FIGS. 4 and 5 to define eight generally sharp post edges 70 per each post 62. The difference is related to a method by which the portion 58 is formed and will be described in detail later. The post edges 70 preferably extend generally perpendicular to the inner attachment surface portion 66. The side attachment surfaces 68 are radiused as before at their intersections 72 with the concave surface parts 60.

The methods by which portions 24, 40 and 58 are formed will next be described by reference to FIG. 8 in conjunction with FIGS. 2, 4 and 6, respectively. Referring first to FIG. 8, there is schematically shown the implant 10 and apparatus for forming portions 24, 40 and 58 on the implant 10. The apparatus is all conventional and includes a laser 74, a power supply 76 for the laser 74, optical elements 78 for focusing and/or directing a beam of energy emitted from the laser 74 onto the implant 10, apparatus 80 for positioning the optical elements 78 relative to the implant 10, apparatus 82 for positioning the implant 10 relative to the optical elements 78, controls 84 for the positioning apparatus 80 and controls 86 for the positioning apparatus 82. The laser 74 can be of many conventional types including carbon dioxide lasers, neodymium:glass lasers, neodymium:yttrium aluminum garnet (Nd:YAG) lasers, and argon lasers. A laser beam 75 is directed at the implant 10 to form the attachment surface 22 embodied as portions 24, 40 and 58.

A particular advantage of laser processing relates to the extremely rapid cooling rates of the remaining non-vaporized material. Cooling rates on the order of 1,000,00020 C./sec. Are common with laser surface modifications. The rapid cooling rate not only minimizes the effects of the surface modification on the bulk of the material, but also results in a surface region of extremely fine grain size, which may be considered nearly amorphous. Microhardness measurements of the laser-textured cobalt-chrome alloy described in Example 1 below demonstrated an increase in hardness from a diamond microhardness number of about 350 (approximately 35 Rockwell C) in the bulk material to a diamond microhardness number of about 520 (approximately 50 Rockwell C) in the surface region melted by the laser. Thus, the extremely fine grain size obtained from laser processing results in improved physical properties of the surface and might also be associated with improved corrosion resistance, which is a known characteristic of amorphous metals.

A method by which portion 24 can be formed is illustrated by arrows A and B shown in FIG. 2. The laser beam 75 was first focused on the portion 24 directly in front of arrow A for a predetermined period of time, and a first cylindrical bore 88 was drilled. The laser beam 75 was moved a predetermiend distance in the direction of the arrow A, and a second cylindrical bore 90 was drilled. Movement of the laser beam 75 relative to the implant 10 was conventionally accomplished by the apparatus 80, the apparatus 82, the controls 84 and the controls 86. The diameters of the bores 88 and 90 were greater than the distance the beam 75 was moved so that the bores 88 and 90 intersected and formed the rim 30 as described earlier. The method was repeated first along line A and later along line B in an interlacing pattern to form the inner attachment surface portion 32. Along line B, the distance the laser beam 75 was moved between bores was approximately doubled to form the posts 28.

The radiused intersections 38 were formed by melting and vaporizing localized areas of the surface 22 using the laser beam 75. The final configuration of the surface 22 is due to a combination of the effects of laser drilling as shown in FIG. 9 and FIG. 10. These effects include surface tension in the melted material, the beam intensity profile, beam reflection off the side attachment surfaces, and material vaporization. While the exact mechanism of forming the final configuration of the radiused intersections 38 is not precisely known, it is the repeatable and reproducible result of laser drilling as described.

Alternative embodiment portions 40 and 58 were similarly formed. In the case of portion 40, the posts 44 are relatively smaller and more closely spaced than the posts 28 of FIG. 2 and the smaller posts 44 were therefore apparently more affected by the complex effects of laser drilling. As a result, the posts 44 tend to have more fully radiused post edges 54 and also have a bulbous protrusion 46 at the free end of each post 44. The mechanism of forming the final configuration of the smaller and more closely spaced posts 44 is not known precisely, but appears to be related to surface tension effects in the melt, melt flow and resolidification of the rim entrance, increased material removal due to decreased reflectance, increased material removal due to reflectance off the side attachment surfaces, effects of expanding vapor forces, and recondensation of ejected material on the entrance rim. The bulbous protrusions 46 at the free end of each post 44 have a distinct advantage in enabling mechanical interlocking at the interface that will resist forces normal to the implant surface 22. The more fully radiused post edges 54, on the other hand, enable less mechanical interlocking to resist torsional forces. Clearly, the relative important of these different effects must be considered in selecting the appropriate surface structure for a given implant application.

The third embodiment portion 54 of FIG. 6 was formed by the method used in relation to FIG. 4 except that the lines of bores were spaced apart approximately three times the distance between successive bores and the lines were crisscrossed by a second series of lines of bores as indicated by arrows C and D, respectively. The parallel spacing between successive lines of bores on line C and between successive lines of bores on line D are shown to be approximately the same but it need not be to produce a suitable attachment surface 22.

Many other embodiments can be formed by conventional adjustment of the apparatus 80 and 82. For example, the number of side attachment surfaces per post can be varied. Also, the intensity of the laser beam can be changed to affect the size, shape and location of the protrusions on the posts, and the angle at which the posts project from the inner attachment surface can be varied. Finally, noncircular laser beams can be used. For example, a square-shaped beam can be used. It appears that a square beam would lessen the bore-to-bore spacing needed to create sutiable posts, and the resultant intersecting rims would be shorter than those formed by a circular beam of the same intensity. It further appears that posts formed by a square-shaped laser beam would have less concave side attachment surfaces than posts formed by a circular beam. Other suitable beam shapes appear to include triangular, hexagonal and other polygonal shapes.

Using the above-described methods, the following attachment surfaces were formed on the following implants.

EXAMPLE 1

A neodymium: YAG, pulsed laser available from Raytheon as Model No. SS-500 in an HDE Systems unit was used to form the attachment surface shown in FIG. 2 and FIG. 3 as the portion 24. The laser was set at a pulse length of 1.2 milliseconds and a pulse rate of 20 pulses per second. The power was set at 20.0 watts which, when combined with a pulse rate of 20 pulses per second, produced an average energy of 1.0 Joule per pulse. A 5 centimeter focal length lens was used. The beam was focused about 0.64 millimeters below the surface of an implant. The implant was a stemmed femoral component comprised of a cobalt and chrome alloy as previously described.

The portion 24 was formed by first drilling the bores along the lines of arrow A of FIG. 2. The laser moved at a scan speed of 25.4 centimeters per minute. At the end of each straight line portion of arrow A, the laser was stepped about 0.51 millimeters perpendicular to the last-formed line portion, and a new line portion formed. The new line portion was maintained parallel to the last line portion. Next, the bores along the lines of arrow B were formed similarly. The starting point was offset about 0.25 millimeters from the starting point of arrow A, the scan speed was increased to 61.0 centimeters per minute and the step size was maintained at about 0.51 millimeters. The total area scanned was about 1.5 centimeters by 2.5 centimeters.

The average bore depth was about 320 microns. The drilling of bores along the lines of arrows A and B resulted in a distance between facing side attachment surfaces 34 of about 250 microns. The multiplicity of elongate posts 28 each had a transverse width of about 250 microns.

EXAMPLE 2

A neodymium:glass laser available from Laser Inc., a subsidiary of Coherent Inc., as Model No. 11D was used with another stemmed femoral component comprised of a cobalt and chrome alloy as before. The attachment surface shown in FIGS. 4 and 5 was formed on the implant. The laser was set at a pulse length of 1.0 millisecond and was manually pulsed a single shot at a time. The energy per pulse was 0.5 Joules. A 6.4 centimeter focal length lens was used. The beam was focused on the surface of the implant.

The portion 40 was formed by drilling the bores along the line of FIG. 4 by manually positioning a micrometer-driven X-Y stage. Between successive bores and at the end of each straight line portion of the arrow, the laser was stepped about 0.25 millimeters. The total area scanned was about 2 millimeters by 4 millimeters.

The average bore depth was about 1000 microns. The distance between facing side attachment surfaces 52 was in the range of about 100–200 microns. The multiplicity of elongate posts 44 each had a transverse width of about 150 microns.

EXAMPLE 3

The neodymium:YAG, pulsed laser of Example 1 was used with another stemmed femoral component comprised of a cobalt and chrome alloy as before. The attachment surface shown in FIGS. 6 and 7 was formed on the implant. The laser was set at a pulse length of 1.2 milliseconds and a pulse rate of 20 pulses per second. The power was set at 20.0 watts which produced an average energy of 1.0 Joule per pulse. The beam was focused about 0.64 millimeters below the surface of the implant.

The portion 58 was formed by first drilling the bores along the lines of arrow C of FIG. 6. The laser moved at a scan speed of 25.4 centimeters per minute. At the end of each straight line portion of arrow C, the laser was stepped about 0.76 millimeters perpendicular to the last-formed line portion, and a new line portion formed. The method was repeated along the lines of arrow D to create a crisscross pattern. The total area scanned was about 1.5 centimeters by 2.5 centimeters.

The average bore depth was in the range of about 300–700 microns. The distance between facing side attachment surfaces 68 was about 250 microns. The multiplicity of posts 62 each had a transverse width of about 500 microns.

EXAMPLE 4

A carbon dioxide, pulsed laser available from Coherent Inc. as Model No. 525 was used to form an attachment surface on ultrahigh molecular weight polyethylene, which is a commonly used material for the acetabular component of hip prostheses. The attachment surface formed on the implant was similar to that shown in FIGS. 2 and 3. The laser was set at a pulse length of 1 millisecond and a pulse rate of 10 pulses per second. The power was set at 5 watts which, when combined with a pulse rate of 10 pulses per second, produced an average energy of 0.5 Joules per pulse. A 12.7 centimeter focal length lens was used in combination with a 2X beam expander. The beam was focused on the surface of the implant.

A portion 24 was formed by drilling bores in a pattern similar to Example 1. The laser moved along line A at a scan speed of 2.03 centimeters per minute and was stepped 0.51 millimeters between lines. The bores along line B were similarly formed starting from a position offset 0.25 millimeters from line A with a scan speed of 40.6 centimeters per minute and the step size maintained at 0.51 millimeters. The total area scanned was about 6 millimeters by 6 millimeters.

Laser drilling of plastic materials, as compared with metallic materials, is considerably more difficult. Plastic materials are generally more likely to melt and less likely to vaporize. Using the described method, the drilling of bores along the lines of arrows A and B resulted in a distance between facing side attachment surfaces 34 of about 220 microns. The multiplicity of elongate posts 28 each had a transverse width of about 440 microns. The average bore depth in this sample was not measured, but appeared to be on the order of 500 microns.

EXAMPLE 5

The neodymium:glass laser of Example 2 was used with another stemmed femoral component comprised of a titanium-6 aluminum-4 vanadium alloy, which is commonly used for implants. An attachment surface similar to that shown in FIGS. 2 and 3 was formed on the implant. The laser was set at a pulse length of 1.0 millisecond and was manually pulsed a single shot at a time. The energy per pulse was 0.5 Joules. A 6.4 centimeter focal length lens was used in conjunction with a 2 mm aperture located between the lens and the laser output mirror. The beam was focused on the surface of the implant.

A portion 24 was formed by drilling bores in a pattern similar to Example 1, except individual bores were drilled a single shot at a time as in Example 2. The individual bores were spaced 0.2 millimeters apart by manually positioning a micrometer-driven X-Y stage. At the end of each straight line portion A, the laser was stepped about 0.4 millimeters perpendicular to the last-formed line portion and a new line portion was formed. The new line portion was maintained parallel to the previous line portion. Next, the bores along lines B were formed similarly. The starting point was offset about 0.2 millimeters from line A and the spacing of individual bores was doubled to about 0.4 millimeters. The step size between lines was maintained at about 0.4 millimeters. The total area scanned was approximately 2 millimeters by 4 millimeters.

The drilling of bores along the lines of arrows A and B resulted in a distance between facing side attachment surfaces 34 of about 220 microns. The multiplicity of elongate posts 28 each had a transverse width of about 220 microns. The average bore depth was not measured in this sample, but appeared to be on the order of 500 microns.

What is claimed is:

1. A method of forming an attachment surface on an implant for use in a human body, said method comprising the steps of:
   a. directing a pulsating beam of laser energy towards a surface of the implant;
   b. focusing said beam of laser energy at a distance below said surface of said implant;
   c. moving said beam of laser energy relative to said surface in a first direction at a first speed to drill a first multiplicity of generally cylindrical bores having a diameter in the range of about 50–400 microns with adjacent bores having center-to-center spacings less than the sum of the radiuses of said adjacent bores, so that the rims of said adjacent bores intersect below said surface of said implant; and
   d. moving said beam of laser energy relative to said surface in a second direction generally parallel to said first direction at a second speed greater than said first speed to drill a second multiplicity of generally cylindrical bores in said surface, each of said bores having a diameter in the range of about 50–400 microns with adjacent bores having center-to-center spacings greater than the sum of the radiuses of said adjacent bores, said second direction being perpendicularly spaced from said first direction less than the sum of the radiuses of one of said bores of said first multiplicity and one of said bores of said second multiplicity, so that the rims of said ones of said bores intersect below said surface of said implant to define an inner attachment surface within said implant and a multiplicity of spaced posts projecting from said inner attachment surface portion.

2. The method of forming an attachment surface according to claim 1 wherein said second speed is about twice said first speed.

3. The method of forming an attachment surface according to claim 2 wherein said beam of laser energy is powered at about one Joule per pulse.

4. The method of forming an attachment surface according to claim 2 wherein said beam of laser energy is provided by a neodymium:YAG or a neodymium:-glass laser operated at a 1.06 micron wavelength.

5. A method of forming an attachment surface on an implant for use in a human body, said method comprising the steps of:
   a. pulsing a beam of laser energy at a first pulse rate;
   b. directing said beam of laser energy towards a surface of said implant;
   c. focusing said beam of laser energy at a distance below said surface of said implant;
   d. moving said beam of laser energy relative to said surface in a first direction to drill a first multiplicity of generally cylindrical bores having a diameter in the range of about 50–400 microns with adjacent bores having center-to-center spacing less than the sum of the radiuses of said adjacent bores so that the rims of said adjacent bores intersect below said surface of said implant;
   e. pulsing said beam of laser energy at a second pulse rate higher than said first pulse rate;
   f. moving said beam of laser energy relative to said surface in a second direction generally parallel to said first direction to drill a second multiplicity of generally cylincrical bores in said surface, each of said bores having a diameter in the range of about 50–400 microns with adjacent bores having center-to-center spacings greater than the sum of the radiuses of said adjacent bores, said second direction being perpendicularly spaced from said first direction less than the sum of the radiuses of one of said bores of said first multiplicity and one of said bores of said second multiplicity, so that the rims of said ones of said bores intersect below said surface of said implant to define an inner attachment surface within said implant and a multiplicity of spaced posts projecting from said inner attachment surface portion.

6. The method of forming an attachment surface according to claim 5 wherein said second pulse rate is about half said first pulse rate.

7. The method of forming an attachment surface according to claim 6 wherein said beam of laser energy is powered at about one Joule per pulse.

8. The method of forming an attachment surface according to claim 7 wherein said beam of laser energy is provided by a neodymium:YAG or a neodymium:-glass laser operated at a 1.06 micron wavelength.

* * * * *

UNITED STATES PATENT AND TRADEMARK OFFICE
CERTIFICATE OF CORRECTION

PATENT NO. : 4,673,409
DATED : June 16, 1987
INVENTOR(S) : Craig L. Van Kampen & Eric N. Hockert It is certified that error appears in the above—identified patent and that said Letters Patent is hereby corrected as shown below:

Col. 1, line 25, "questoins" should read --questions--.
Col. 1, line 60, "the" should read --The--.
Col. 3, line 28, "regions" should read --region--.
Col. 6, line 41, "surfaces 63" should read --surfaces 68--.
Col. 7, line 8, "1,000,00020 C./sec." should read --1,000,000° C/sec.--
Col. 11, line 44, "according to claim 2" should read --according to claim 3--.
Col. 7, line 8, "Are common" should read --are common--.
Coversheet, Inventor: "Craig L. Van Kampen" should read --Craig L. Van Kampen and Eric N. Hockert--.

Signed and Sealed this

Tenth Day of November, 1987

Attest:

DONALD J. QUIGG

Attesting Officer

Commissioner of Patents and Trademarks